(12) United States Patent
Ciupik et al.

(10) Patent No.: US 8,556,975 B2
(45) Date of Patent: Oct. 15, 2013

(54) DEVICE FOR SURGICAL DISPLACEMENT OF VERTEBRAE

(75) Inventors: Lechoslaw Ciupik, Zielona Gora (PL); Marek Szpalski, Brussels (BE); Robert Gunzburg, Berchem (BE); Daniel Zarzycki, Zakopane (PL); Jerzy Pieniazek, Bytom (PL)

(73) Assignee: LFC SP. Z.O.O., Zielona Gora (PL)

( * ) Notice: Subject to any disclaimer, the term of this patent is extended or adjusted under 35 U.S.C. 154(b) by 207 days.

(21) Appl. No.: 12/889,314

(22) Filed: Sep. 23, 2010

(65) Prior Publication Data

US 2011/0077738 A1    Mar. 31, 2011

(30) Foreign Application Priority Data

Sep. 28, 2009  (PL) .......................................... 389148

(51) Int. Cl.
*A61F 2/44* (2006.01)
(52) U.S. Cl.
USPC ................. 623/17.15; 623/17.11; 623/17.16; 606/90; 606/105
(58) Field of Classification Search
USPC .............. 623/17.11–17.16; 81/155, 165, 170; 606/90, 105, 328
See application file for complete search history.

(56) References Cited

U.S. PATENT DOCUMENTS

| | | | |
|---|---|---|---|
| 5,653,762 A | 8/1997 | Pisharodi | |
| 6,416,551 B1 * | 7/2002 | Keller | 623/17.11 |
| 6,491,695 B1 | 12/2002 | Roggenbuck | |
| 6,533,791 B1 | 3/2003 | Beetz et al. | |
| 7,211,112 B2 * | 5/2007 | Baynham et al. | 623/17.11 |
| 7,744,649 B2 * | 6/2010 | Moore | 623/17.11 |
| 2004/0073214 A1 | 4/2004 | Mehdizadeh | |
| 2004/0254644 A1 * | 12/2004 | Taylor | 623/17.13 |
| 2005/0234555 A1 * | 10/2005 | Sutton et al. | 623/17.15 |
| 2006/0149383 A1 * | 7/2006 | Arnin et al. | 623/17.13 |
| 2007/0055374 A1 | 3/2007 | Copf, Jr. | |
| 2007/0123898 A1 | 5/2007 | Squires et al. | |
| 2007/0123989 A1 | 5/2007 | Gfeller et al. | |
| 2007/0260317 A1 * | 11/2007 | Ankney et al. | 623/17.16 |
| 2007/0270968 A1 * | 11/2007 | Baynham et al. | 623/17.11 |
| 2008/0033440 A1 | 2/2008 | Moskowitz et al. | |
| 2008/0051902 A1 * | 2/2008 | Dwyer | 623/17.16 |
| 2008/0319481 A1 | 12/2008 | Moore | |
| 2009/0125062 A1 | 5/2009 | Arnin | |

FOREIGN PATENT DOCUMENTS

| | | |
|---|---|---|
| DE | 19750382 A1 | 5/1999 |
| WO | 96/40016 A2 | 12/1996 |
| WO | 2005/082292 A1 | 9/2005 |
| WO | 2007/048012 A2 | 4/2007 |

* cited by examiner

*Primary Examiner* — Kevin T Truong
*Assistant Examiner* — Tracy Kamikawa
(74) *Attorney, Agent, or Firm* — Venable, Campillo, Logan & Meaney PC

(57) ABSTRACT

A device for use as an implant for surgical displacement of vertebrae, and that is comprised of two parts co-working in a sliding way: a sliding part with an internal thread and a carrier part, and also a driving element with an external thread which is located between the parts, is described. The driving element includes a head and the sliding part of the device includes a threaded guideline cooperating with the driving element and a seat of a diameter corresponding with the head's diameter and length greater than the head's length, and the carrier part has a seat of a diameter and length corresponding with the head's diameter and length.

15 Claims, 4 Drawing Sheets

DEVICE FOR SURGICAL DISPLACEMENT OF VERTEBRAE

The present invention claims priority under 35 U.S.C. 119 (a)-(d) through one or more of the treaties listed in MPEP 201.13 for an application and registration under the Polish Patent Office Application No. P-389148 having a filing date of 28 Sep. 2009 in the Polish Patent Office of the Republic of Poland (Urząd Patentowy Rzeczypospolitej Polskiej (UPRP)) located in Warsaw, Poland and said foreign priority document, Application No. P-389148, and any other documents to which this application claims priority are hereby incorporated by reference.

FIELD OF THE INVENTION

This invention relates to surgical displacement of vertebrae, which is applied in surgical treatment of spondylolisthesis.

BACKGROUND

Literature data indicate that sliding of vertebrae occurs on average in 10% of patients treated because of back pain. This pathology may cause a significant disability, both among the youth and adults. Surgical treatment of spondylolisthesis is provided when neurological symptoms and/or pain occur, or even increase, even though conservative treatment had been previously administered. Until now in medical practice, the most commonly used treatment has consisted in bringing the spine to spinal fixation by bone fusion on the sliding level. The spondylodesis itself is not always a sufficient means and does not bring positive results in the form of: restoration of proportions in the height of disc space, thereby reconstruction of the correct geometry, reduction of posture deformation, removal of pain discomfort, restoration of biomechanical balance. To achieve all of the above mentioned benefits, decompression of nerve structures and reposition of the displaced vertebra is essential.

Devices for spondylolisthesis reposition are known; most of all they are based on different kinds of pulling screws or special repositioning constructions, whose principal feature is a considerably large number of elements and surgical difficulties resulting from the complexity of the system removing this pathology.

Their application often involves extensive surgical actions, which significantly increase patient's burden and can lead to intra- and postoperative complications.

An implant, apparatus and a method for spondylolisthesis correction are known from the patent application WO 96/40016. The implant is in the form of one-element cage intended for blocking the dislocation of vertebrae, whereas the correction itself is performed with a specially designed apparatus introduced into the intervertebral space, including a longitudinal body composed of two elements, which by moving along each other, align the dislocated vertebrae. The disadvantage of this solution is the possibility of losing reposition during replacement of the corrective apparatus with the locking cage.

An apparatus and a method for the realignment and stabilization of adjacent vertebrae are known from the patent application US 2008/0319481. The implant has two halves which are interlocked so that they can slide horizontally with respect to each other. The movement of the implant halves and their respective positions are controlled by a screw set within the implant. The implant includes radial anchors which fit into alignment slots made in the misaligned vertebra. The screw set in the implant is used to advance the halves of the implant which in turn move the misaligned vertebrae back into correct positions. The solution provides for the correction of spondylolisthesis only by means of using the anterior surgical approach, which due to the possibility of disturbing important anatomic structures situated there, seriously hinders and sometimes prevents surgical activities and may pose considerable risk to the patient related; for example, to the prolonged duration of surgery. Another disadvantage of this solution is also the necessity of making an incision—with the use of a special instrument—for slots in the vertebral body for anchors. Yet another drawback is the complicated and difficult to control procedure of introducing the implant into the interbody space, requiring adapting its position to the slots prepared earlier. The screw gear employed allows movement only in one direction in the direction of the reposition of dislocated vertebrae. As there is no reverse mechanism, intraoperative correction and implant's removal are prevented, resulting in patient risk. Guiding employed in the form of a dove tail does not have any protection against locking of the shift due to the fact that the cooperating implant halves become distant from each other as a result of the elbowing action of the screw. Fixation of vertebrae position and locking of the implant itself require using additional means in the form of a nut and an additional fixing plate, and this increases the number of implant elements and moreover, irritates tissues.

An interbody spacer is known from the patent application US 2007/0123989 intended for surgical treatment of spondylolisthesis. The spacer is composed of two halves and a locking screw gear, installed using the anterior approach between two vertebrae and anchored in the vertebral body with bone screws in a variant connected with a reduction plate. In the disclosed embodiment, correction of spondylolisthesis is made by manipulating the adjusting mechanism in such a way that the first and the other half move along each other, thus aligning the vertebrae. The locking screw gear may have a central screw, which at rotation can move one of the halves forward or backward. In one embodiment of the screw gear, it can be a central rail allowing the movement of both halves forward and backward, and the mechanism can be secured by a lateral blockage. The adjusting mechanism employed does not offer the possibility of moving the halves along each other in opposite directions. Another disadvantage of this solution is the mechanism of anchoring the interbody spacer in the vertebral body, which does not provide a secure fixation during reposition and causes spacer's elements to project from vertebral margins after reduction of pathology, thus endangering biological structures situated in this area.

SUMMARY

Free of the above mentioned inconveniences is a device comprising an implant for surgical displacement of vertebrae, which is composed of two parts co-working in a sliding way: a sliding part with an internal thread and a carrier part, and also a driving element with an external thread which is located between the parts. According to the invention, the driving element is provided with a head, whereas the sliding part of the device is equipped with a threaded guideline cooperating with the driving element and a seat of a diameter corresponding with the head's diameter and length greater than the head's length, and the carrier part has a seat of a diameter and length corresponding with the head's diameter and length. Furthermore, the sliding part and the carrier part are provided with cooperating shaped elements, which form a lock preventing separation of both parts in the direction perpendicular to the device longitudinal axis during performance of corrective actions. The lock is formed by at least one element, which is located in the sliding part and one element in the carrier part. In one embodiment of the device, the element of the lock located in the sliding part of the device is in the form of a cylinder. In another embodiment, the shaped element is in the form of a fragment of a cuboid.

The threaded guideline in the sliding part and carrier part is in the form of a sleeve. Preferably, this sleeve can be open longitudinally.

The external surface of the sliding part and carrier part is provided with drive-anchoring elements, which are in the form of shelves provided with resistance surfaces and at least one shaped cutting knife. In one embodiment of the device, the drive-anchoring elements are provided with gaps. In another embodiment, at least one shelf is articulated with a shaped seat on the external surface of the device. Preferably, the movable shelf is provided with a resistance projection. The drive anchoring elements, which constitute the outfit of the external part of the device's sliding part, are located at an angle of 0 up to 100°, and the drive-anchoring elements of the carrier part are situated at an angle of 0 up to 100° in relation to the external surface.

The device for the treatment of spondylolisthesis by surgical displacement of vertebrae according to the invention is characterized in that it has a simple and compact construction limiting the area of surgical intervention, thus invasiveness of the procedure is decreased. It enables surgeries to be performed both using the posterior and anterior approach, depending on medical needs and recommendations. At the same time, it ensures decompression of compressed nerve structures, restoration of correct anatomical proportions and final blocking of the whole system, preventing secondary slippage without any additional accompanying elements, and this in turn decreases the risk related to the necessity of cooperation of all the elements of the stabilizing system.

The construction of the threaded guideline of the motion driving element according to the invention secures the drive-repositioning system against blocking, thus increasing the safety of the displacement of vertebrae being performed.

A simple and safe seating of the implant in the interbody space shortens the duration of surgery and minimizes patient's burden, increasing his safety. The construction of the implant satisfies biomechanical requirements for stabilization and is adapted to the anatomical shape of the interbody space, which ensures effectiveness of treatment of patients at any age.

BRIEF DESCRIPTION OF THE DRAWINGS AND DETAILED DESCRIPTION

The invention is preferrably disclosed in examples of implementation in the accompanying figures, where FIG. 1 illustrates the device in a section with a visible driving element and drive-anchoring elements in the form of shelves equipped with shaped cutting knives and with a lock;

Figure 1:
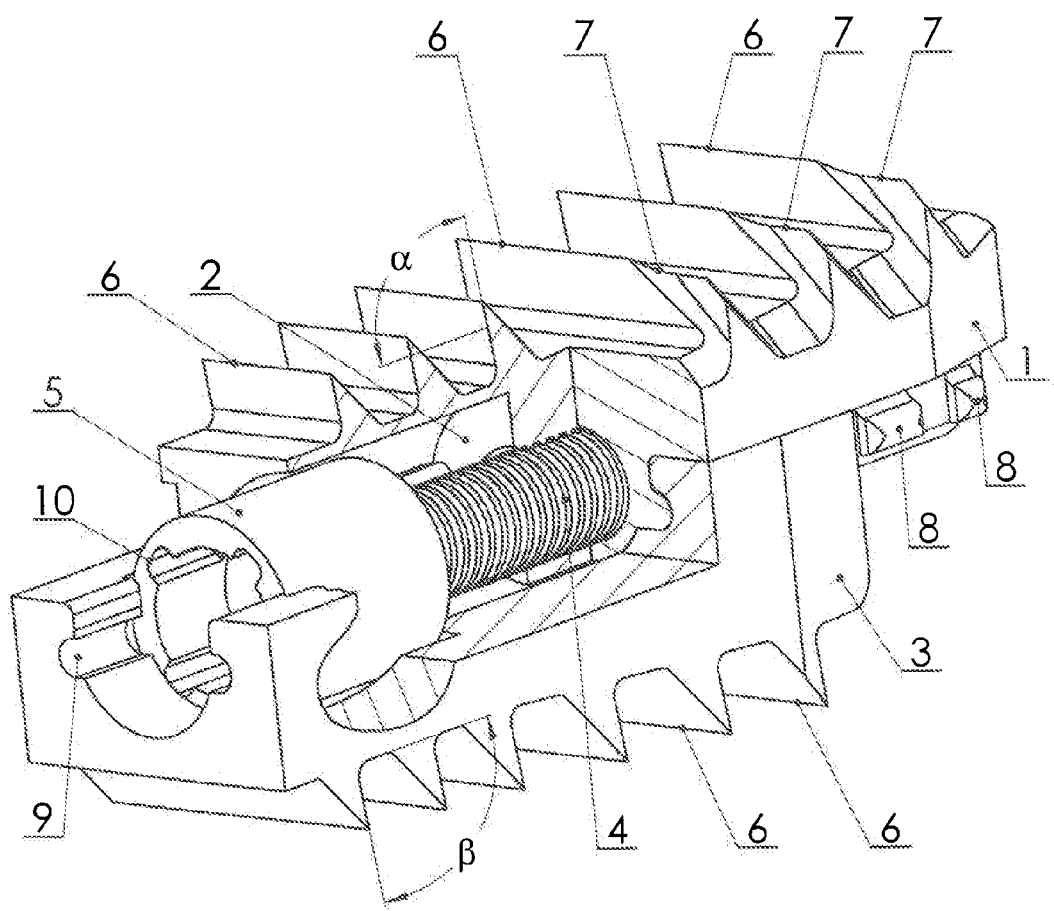

The device presented in FIG. 1 is composed of a sliding part 1 with a threaded guideline 2, a carrier part 3 and driving element 4 with an external thread provided with a head 5. Sliding part 1 and carrying part 3 of the device are provided on the external surface with drive-anchoring elements 6. Drive-anchoring elements 6 on device's sliding part 1 are in the form of shelves provided with resistance surfaces and shaped cutting knives 7. Sliding part 1 is also provided with at least two shaped elements 8 (also known as a first shaped element) in the form of cylinder's fragments constituting together with a shaped element 9 (also known as a second shaped element) in device's carrier part 3 a lock, preventing their separation in the perpendicular direction to the longitudinal axis of the device. Head 5 of the driving element 4 is provided with manipulative elements 10 assigned for cooperation with the installation instrument.

Figure 2:
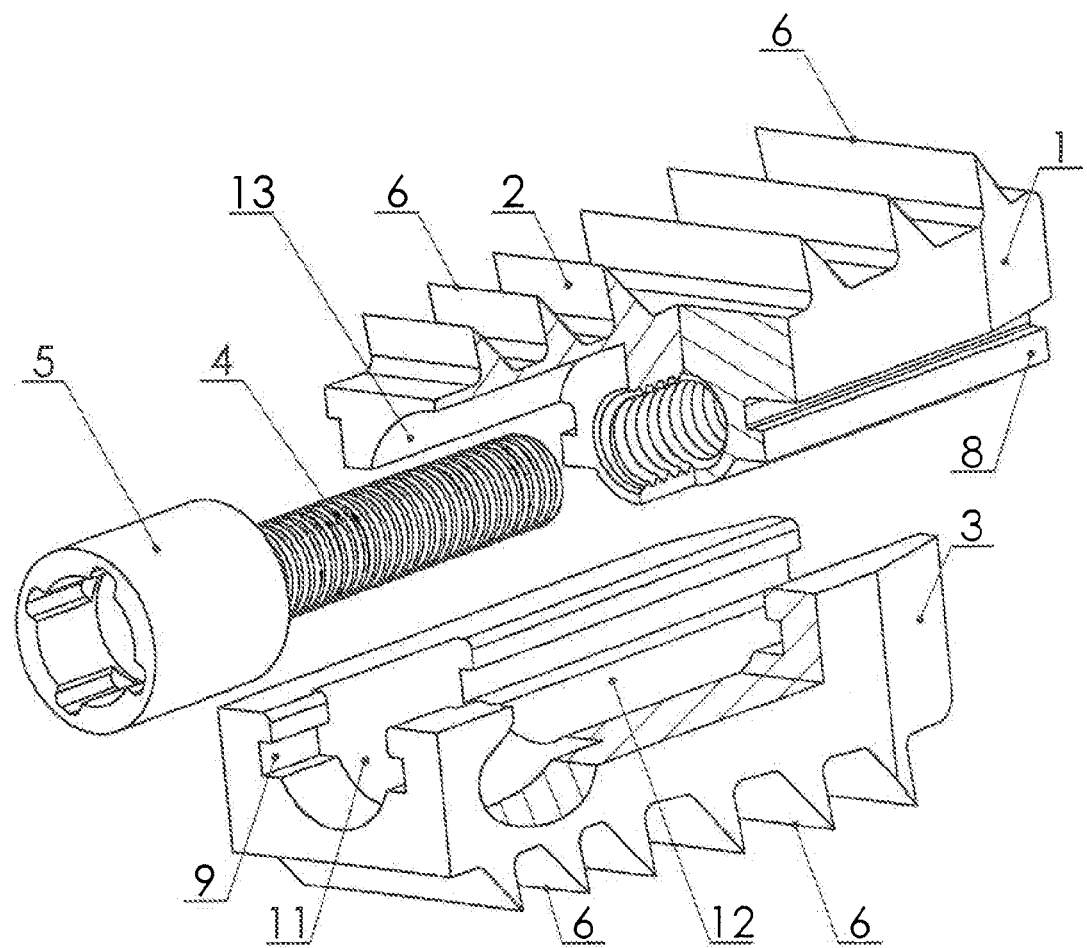
FIG. 2 shows the device in an arrangement with a threaded guideline in the shape of a sleeve and with drive-anchoring elements in the form of uniform shelves.

The device shown in an arrangement in FIG. 2 is provided on the external surface with drive-anchoring elements 6 in the form of uniform shelves. Carrier part 3 of the device is provided with a cylindrical seat 11, shaped element 9 being an element of the lock and longitudinal gap 12 corresponding by shape with the threaded guideline 2 cooperating with it. Cylindrical seat 11 cooperating with the head 5 of the driving element 4 has got the diameter and length corresponding with the diameter and length of head 5. Sliding part 1 of the device is provided with a cylindrical seat 13 with diameter corresponding with the diameter of head 5 and length longer than head's 5 length and with the shaped element 8 being an element of the lock in the form of cuboid's fragment. Threaded guideline 2 is in the form of a sleeve.

Figure 3:
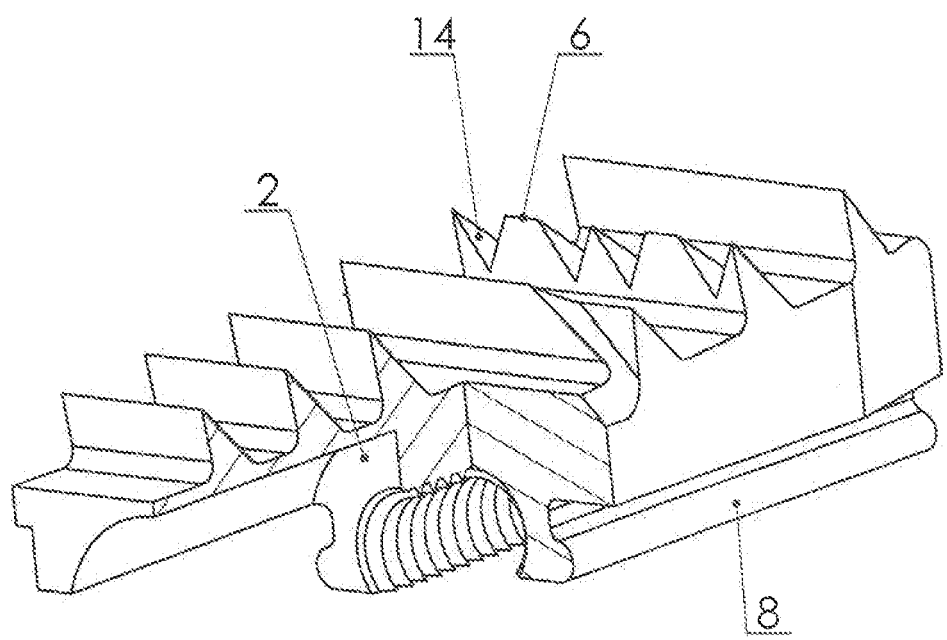
FIG. 3 illustrates the sliding part with a threaded guideline in the form of an open sleeve and with a shelf provided with gaps.

In another embodiment presented in FIG. 3, threaded guideline 2 in the sliding part 1 is in the form of a longitudinally opened sleeve, shaped projection 8 in the form of cylinder's fragment, and the external surface of the sliding part 1 is provided with the drive-anchoring element 6 with gaps 14.

Figure 4:
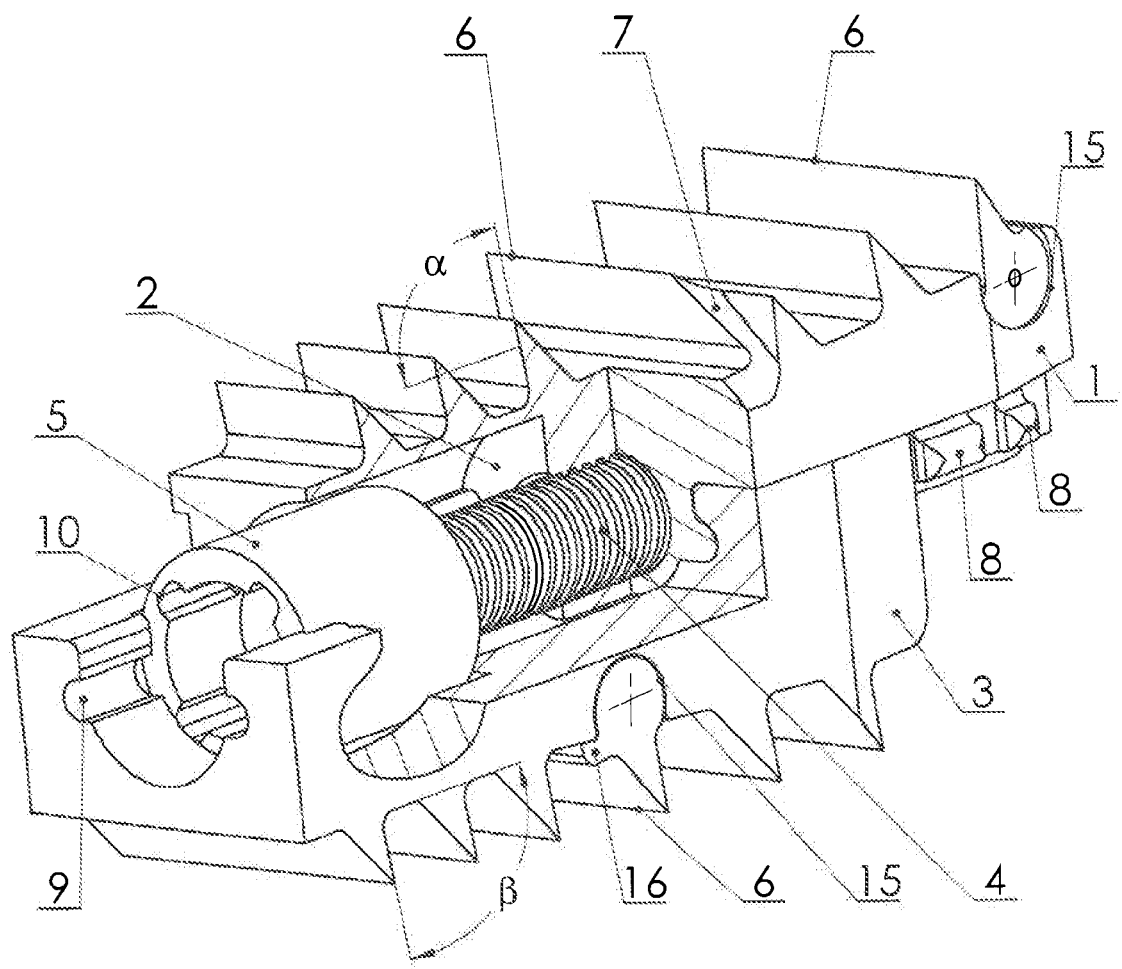
FIG. 4 shows an embodiment of the device with drive-anchoring elements in the form of movable shelves on the sliding part and the carrying part (also known as the carrier part).

In the embodiment shown in FIG. 4, the device has got two drive-anchoring elements 6 articulated with a shaped seat 15 on the external surface of the sliding part 1 and carrier part 3 of the device. One of drive-anchoring elements 6 is provided with a resistance projection 16 preventing uncontrolled rotation of the shelf.

FIGS. 1-4 show that the sliding part includes a first contact face that extends parallel to the longitudinal axis of the device, the carrier part includes a second contact face that extends parallel to the longitudinal axis of the device and contacts the first contact face, where the driving element imparts movement of the sliding part relative to the carrier part along the longitudinal axis of the device such that the sliding takes place along the contact faces.

Thus, specific embodiments and applications of the device for a surgical displacement of vertebrae have been disclosed. It should be apparent, however, to those skilled in the art, that many more modifications besides those already described are possible without departing from the inventive concepts herein. The inventive subject matter, therefore, is not to be restricted expect in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps can be present, or utilized, or combined with other elements, components, or steps that are not expressly referenced. Where the specification or claims, if any, refer to at least one of something selected from the group consisting of A, B, C . . .

and N, the text should be interpreted as requiring only one element from the group, no A plus N, or B plus N, etc.

What is claimed is:

1. A device for surgical displacement of vertebrae, comprising:
   a sliding part with an internal thread;
   a carrier part, wherein the sliding part and the carrier part cooperate in a sliding way; and
   a driving element with an externally threaded portion, the driving element located between the sliding part and the carrier part;
   wherein the driving element includes a head having a diameter larger than a diameter of the externally threaded portion and a length shorter than a total length of the driving element;
   wherein the internal thread of the sliding part acts as a threaded guideline in a longitudinal axis of the device cooperating with the driving element to impart a movement of the sliding part relative to the carrier part along the longitudinal axis of the device;
   wherein the sliding part includes a seat having a diameter corresponding with the diameter of the head;
   wherein the seat has a length larger than the length of the head and shorter than the total length of the driving element;
   wherein the carrier part includes a cylindrical seat with a diameter and a length corresponding to the diameter and the length of the head;
   wherein the sliding part includes a first contact face that extends parallel to the longitudinal axis of the device, the carrier part includes a second contact face that extends parallel to the longitudinal axis of the device and contacts the first contact face, where the sliding takes place along the first and second contact faces;
   wherein the sliding part and the carrier part include cooperating elements, respectively: at least one first shaped element and at least one second shaped element; and
   wherein the cooperating elements extend parallel to the longitudinal axis of the device and prevent separation of the sliding part and the carrier part in a perpendicular direction to the longitudinal axis of the device.

2. The device according to claim 1 wherein the threaded guideline in the sliding part of the device is in a form of a sleeve.

3. The device according to claim 2 wherein the threaded guideline in the sliding part of the device is in a form of a longitudinally open sleeve.

4. The device according to claim 1 wherein the at least one first shaped element is in a form of a cylinder's fragment.

5. The device according to claim 1 wherein the at least one first shaped element is in a form of a cuboid's fragment.

6. The device according to claim 1 wherein the carrier part and the sliding part further comprise at least one drive-anchoring element on a respective external surface of the carrier part and the sliding part;

where each of the at least one drive-anchoring element has a triangular cross section in a cross sectional plane running parallel to the longitudinal axis of the device with one side of a triangle formed by the triangular cross section being located at the respective external surface of the carrier part and the sliding part, and a corner of the triangle formed by the triangular cross section being located at a distance from the respective external surface of the carrier part and the sliding part; and where each of the at least one drive-anchoring element includes an edge that runs perpendicular to the cross sectional plane and corresponds to the corner of the triangle formed by the triangular cross section which is located at the distance from the respective external surface.

7. The device according to claim 6 wherein the at least one drive-anchoring element is in a form of shelf provided with resistance areas and at least one shaped cutting knife.

8. The device according to claim 7 wherein the at least one drive-anchoring element is articulated with a shaped seat on the respective external surface of the carrier part and the sliding part and includes a resistance projection.

9. The device according to claim 7 wherein the at least one drive-anchoring element of the sliding part of the device is located at an angle ($\alpha$) of 0° to 110° in relation to the external surface of the sliding part of the device, and the at least one drive-anchoring element of the carrier part of the device is arranged at an angle ($\beta$) of 0° to 110° with relation to the external surface of the carrier part of the device.

10. The device according to claim 6 wherein the at least one drive-anchoring element includes gaps.

11. The device according to claim 10 wherein the at least one drive-anchoring element is articulated with a shaped seat on the respective external surface of the carrier part and the sliding part and includes a resistance projection.

12. The device according to claim 1 wherein the carrier part and the sliding part further include drive-anchoring elements in a form of shelves equipped with shaped cutting knives.

13. The device according to claim 1 wherein the at least one first shaped element in the sliding part of the device extends along the longitudinal axis of the device over an entire length of the threaded guideline.

14. The device according to claim 1 wherein the at least one first shaped element includes a number of first shaped elements in the sliding part of the device, the number of first shaped elements extending along the longitudinal axis of the device and distributed over an entire length of the threaded guideline.

15. The device according to claim 1, wherein the at least one second shaped element in the carrier part of the device extends along the longitudinal axis of the device over an entire length of the carrier part except for the cylindrical seat.

* * * * *